(12) United States Patent
Feinle et al.

(10) Patent No.: US 6,534,539 B2
(45) Date of Patent: Mar. 18, 2003

(54) PHARMACEUTICAL COMPOSITION AND METHOD FOR TREATMENT OF DYSPEPSIA

(75) Inventors: Christine Feinle, Adelaide (AU); Michael Fried, Zurich (CH); Hans Lengsfeld, Basel (CH); Thomas Rades, Dunedin (NZ)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 09/923,077

(22) Filed: Aug. 6, 2001

(65) Prior Publication Data

US 2002/0040049 A1 Apr. 4, 2002

(30) Foreign Application Priority Data

Aug. 9, 2000 (EP) ............................................. 00117088

(51) Int. Cl.[7] ............................................. A61K 31/335
(52) U.S. Cl. ....................................................... 514/449
(58) Field of Search .......................................... 514/449

(56) References Cited

U.S. PATENT DOCUMENTS

| | | |
|---|---|---|
| 4,598,089 A | 7/1986 | Hadvary et al. |
| 4,983,746 A | 1/1991 | Barbier et al. |
| 5,175,186 A | 12/1992 | Barbier et al. |
| 5,399,720 A | 3/1995 | Karpf et al. |
| 6,004,996 A | 12/1999 | Shah et al. |

FOREIGN PATENT DOCUMENTS

| | | |
|---|---|---|
| EP | 185359 | 6/1986 |
| EP | 189577 | 8/1986 |
| EP | 443449 | 8/1991 |
| EP | 524495 | 1/1993 |
| WO | WO 99/34786 | 7/1999 |
| WO | WO 00/09122 | 2/2000 |
| WO | WO 00/09123 | 2/2000 |

OTHER PUBLICATIONS

McNeely et al., Drugs 1998;56(2):241–249.*
Feinle et al., Praxis 1998;87:1817–1820.*
Degen, et al., *Gastroenterology*, vol. 112, No. 4, p. a719 (1997).
Bazaldua, et al., *American Family Physician*, vol. 60, No. 6, pp. 1773–1784 (1999).

* cited by examiner

Primary Examiner—Sreeni Padmanabhan
Assistant Examiner—San-ming Hui
(74) Attorney, Agent, or Firm—George W. Johnston; John P. Parise; Lyman H. Smith

(57) ABSTRACT

The present invention relates to compositions containing lipase inhibitors, e.g. orlistat, and the use of such compositions for treating, reducing or preventing functional dyspepsiaafter ingestion of meals, especially of fat containing or fat rich meals.

16 Claims, No Drawings

PHARMACEUTICAL COMPOSITION AND METHOD FOR TREATMENT OF DYSPEPSIA

SUMMARY OF THE INVENTION

The present invention relates to compositions containing lipase inhibitors, e.g. orlistat, and the use of said compositions for treating, reducing or preventing functional dyspepsia after ingestion of meals, especially of fat containing or fat rich meals.

BACKGROUND OF THE INVENTION

Functional dyspepsia is a condition characterized by sensations of gastric fullness, nausea, bloating, gastric distress, etc., after intake of meals (even small meals), especially after intake of fat containing or fat rich meals. A large number of people are afflicted by this condition, continuously or more regularly in response to fat rich meals or fat rich meal items.

The arrival of lipid in the small intestinal lumen normally causes gastric relaxation, modulation of phasic motor activity, and pancreaticobiliary secretion. However, in patients with functional dyspepsia, lipids often provoke postprandial symptoms. Gastric and pancreatic lipases in the intestinal lumen hydrolyze triglycerides to free fatty acids, which may act on brain centers involved in dyspeptic symptoms.

Surprisingly, it has been found in a clinical model for functional dyspepsia that a lipase inhibitor, preferably orlistat, when administered orally, is useful in the treatment, reduction and prevention of functional dyspepsia. According to the present invention, inhibition of fat digestion reduces the intensity of postprandial dyspeptic symptoms.

DETAILED DESCRIPTION OF THE INVENTION

The present invention relates to compositions containing lipase inhibitors, e.g. orlistat, and the use of said compositions for treating, reducing or preventing functional dyspepsia after ingestion of meals, especially of fat containing or fat rich meals.

Orlistat, a gastrointestinal lipase inhibitor, also known as XENCIAL®, is a known compound useful for the control or prevention of obesity and hyperlipidemia. See, U.S. Pat. No. 4,598,089, issued Jul. 1, 1986, which also discloses processes for making orlistat, and U.S. Pat. No. 6,004,996, which discloses pharmaceutical compositions containing orlistat. Additional pharmaceutical compositions containing lipase inhibitors are described, for example, in International Patent Applications WO 00/09122, WO 00/09123, WO01/19340 and WO01/19378.

Additional processes for the preparation of orlistat are disclosed in European Patent Applications Publication Nos. 185,359, 189,577, 443,449, and 524,495.

The addition of a lipase inhibitor such as orlistat (THL, tetrahydrolipstatin) to a fat emulsion infused into the duodenum reduced the intensity of stomach fullness and sensitivity, nausea and bloating in a clinical model of dyspepsia, that is, gastric distension represented by an inflatable balloon. This finding is very important as a large number of patients with digestive symptoms of unknown cause report that their symptoms frequently occur after ingestion of foods containing fat. Thus, by blocking the first step of intestinal lipid digestion these gastrointestinal symptoms can be aleviated using the compositions and methods of the present invention. Hence, the present invention has important clinical implications for the treatment of a subgroup of patients suffering from dyspepsia related to fat intolerance, in that partial inhibition of fat digestion may be an effective measure to relieve their symptoms. In summary, our data demonstrate the importance of inhibition of fat digestion for the suppression of postprandial symptoms.

The term "lipase inhibitor" refers to compounds which are capable of inhibiting the action of lipases such as gastric and pancreatic lipases. Orlistat and lipstatin as described in U.S. Pat. No. 4,598,089 are examples of potent lipase inhibitors. Lipstatin is a natural product of microbial origin. Orlistat is the result of a hydrogenation of lipstatin. Other lipase inhibitors include a class of compounds commonly referred to as panclicins. Panclicins are analogues of orlistat (Mutoh et al, J. Antibiot., 47(12):1369–1375 (1994)). The term "lipase inhibitor" includes synthetic lipase inhibitors such as those described in International Patent Application WO99/34786 (Geltex Pharmaceuticals Inc.). These polymers are characterized in that they have been substituted with one or more groups that inhibit lipases. The term "lipase inhibitor" also includes pharmaceutically acceptable salts of the foregoing compounds. In addition, the term "lipase inhibitor" includes 2-oxy-4H-3,1-benzoxazin-4-ones which have been described in International Patent Application WO00/40569 (Alizyme Therapeutics Ltd.), e.g. 2-decyloxy-6-methyl-4H-3,1-benzooxazin-4-one, 6-methyl-2-tetradecyloxy-4H-3,1-benzoxazin-4-one, and 2-hexadecyloxy-6-methyl-4H-3,1-benzoxazin-4-one.

In a preferred embodiment, the present invention relates to the use of a lipase inhibitor fortreating, reducing or preventing functional dyspepsia. In particular the invention relates to the use of a lipase inhibitor to reduce the intensity of gastric fullness, nausea, and bloating during and after meal ingestion.

In an especially preferred embodiment of the present invention, the lipase inhibitor is orlistat.

The invention also relates to a method for treating, reducing or preventing functional dyspepsia comprising administering an effective amount of a gastrointestinal lipase inhibitor to a mammal, in particular a human, to reduce the intensity of fullness, nausea, bloating, or gastric distress following ingestion of fat rich meals or fat rich food items.

The preferred lipase inhibitor useful in the disclosed methods and compositions is orlistat. Preferably, the lipase inhibitor is administered orally.

The present invention also contemplates an oral composition for treating or preventing functional dyspepsia comprising an effective amount of a lipase inhibitor, preferably orlistat, and a pharmaceutically acceptable carrier or excipient.

The lipase inhibitor, e.g. orlistat, is administered at a dose of from about 30 to about 720 mg per day, preferably orally, in divided doses two to three times per day, most preferably during ingestion of fat rich foods.

Preferably, the dose of lipase inhibitors ranges from about 60 to about 360 mg, most preferably 360 mg per day Most preferably the lipase inhibitor is administered orally, in divided doses, two, most preferably three, times per day. The subject may be a normal weight, an obese or overweight human.

The lipase inhibiting compositions of the invention are most useful when administered with a meal containing fat. Moreover, an additional benefit of the current invention is that other illnesses such as obesity and associated risk factors such as hypercholesterolemia, diabetes mellitus, etc. (described e.g. in U.S. Pat. No. 4,598,089 and International Patent Application WO98/34630) can be treated in parallel with the treatment of functional dyspepsia.

Orlistat can be administered to humans in conventional oral compositions, such as, tablets, coated tablets, hard and soft gelatin capsules, emulsions or suspensions. Examples of carriers which can be used for tablets, coated tablets, dragées and hard gelatin capsules are lactose, maize starch or derivatives thereof, talc, stearic acid or its salts and the like. Suitable carriers for soft gelatin capsules are, for example, vegetable oils, waxes, fats, semi-solid and liquid polyols and the like. Moreover, the pharmaceutical preparations can contain preserving agents, solubilizers, stabilizing agents, wetting agents, emulsifying agents, sweetening agents, coloring agents, flavoring agents, salts for varying the osmotic pressure, buffers, coating agents or antioxidants. They can also contain still other therapeutically valuable substances. Alternatively, the lipase inhibitors may be administered in form of hard gelatine capsule or chewing tablets. The formulations may conveniently be presented in unit dosage form and may be prepared by any methods known in the pharmaceutical art (see above). Preferably, the lipase inhibitor, e.g. orlistat, may be administered according to the formulation shown in the Examples.

EXAMPLES

Materials and Methods

The reduction of dyspeptic symptoms by lipase inhibitors, particularly orlistat, was shown in human clinical studies that measured functional dyspepsia. Specifically, we measured the reduction of dyspeptic symptoms after administration of orlistat to normal volunteers (healthy subjects without a history of gastrointestinal disease (8 female and 7 male), aged 24–38 years; normal body weight (BMI (kg/m$^2$): females: 21.9±0.4, males: 23.4±0.4) during infusion of a fat emulsion into the duodenum in a clinical model of idopathic dyspepsia (gastric distension). BMI means body mass index.

Fat emulsions (Table 1) were infused intraduodenally via a single-lumen, naso-duodenal polyvinyl tube as described previously (Feinle, AJP2000), while the stomach was distended. Gastrointestinal sensations were assessed by a visual analog questionnaire.

The gastric distension was performed by air through a gastric tube (OD: 3.5 mm, ID: 2.8 mm) which had an ultra-thin, flaccid polyethylene bag (capacity: 1100 ml) tied on to its distal end. The proximal end of the tube was connected via a three-way tap to the measurement and the balloon ports of a gastric barostat.

Studies were performed in a double-blind, placebo-controlled, cross-over fashion in randomised order at least one week apart. The subjects were comfortably seated in an upright position. At first, the minimal distending pressure (MDP) was determined by increasing intragastric pressure in steps of 1 mmHg/min. Pressure was then fixed at MDP and fasting tone recorded until variations in gastric volume were no longer observed. The MDP was 8±1 mmHg and did not differ between study days. After 10 min ('baseline'), duodenal infusion of a fat emulsion commenced at a rate of 1 ml/min and was continued throughout the study. Two isobaric distensions were performed, 15 min apart from each other, by increasing intrabag pressure in steps of 1 mmHg/min, while corresponding volumes were monitored.

Gastrointestinal sensations of hunger, satiation, nausea, abdominal bloating and pressure were rated by the subjects on visual analogue scales (VAS). The VAS consisted of a 10 cm line, with 0 cm representing "sensation not present" and 10 cm "strongest sensation ever felt". Sensations were rated immediately before the start of, and every 5 min during, the duodenal infusions. As soon as the subjects reported discomfort, the distension process was discontinued and the air immediately removed from the bag.

TABLE 1

Composition of the fat emulsions and median of fat droplet size distribution.

|  | LCT | LCT-orlistat |
|---|---|---|
| LCT | 30.0 g | 30.0 g |
| orlistat | — | 240 mg |
| Soy lecithin | 2.25 g | 2.25 g |
| Ethanol | 1.75 g | 1.75 g |
| 0.9% saline | 116.0 g | 116.0 g |
| MPS | 10.5 µm | 8.5 µm |

LCT, soybean oil; MPS, median of particle size distribution.

Fat emulsions with 20 % (w/w) oil were prepared from soybean oil with soy lecithin with, and without, orlistat (table 1). The soy lecithin was completely dissolved in ethanol before the oil was added and shaken to obtain a clear solution. Isotonic saline was then added, and the resulting dispersion was homogenized for 3×1 minute at 39 000 rpm using a homogenizer. Orlistat was completely dissolved in ethanol before the soy lecithin was added. The emulsions were used within one hour of preparation. The particle size distribution of the dispersed oil droplets in the emulsions was determined. The particle size of the emulsions remained unchanged and no signs of creaming were detected. Particle size distribution medians are listed in table 1.

Data Analysis

Changes in gastric tone during duodenal infusions were quantified by calculating differences between mean volumes obtained at MDP during the baseline recording (10 minutes) and during the duodenal infusion.

During distensions, intragastric volumes during consecutive pressure steps were calculated by averaging the volume readings obtained during the last 20 seconds of each pressure step. These data were then used to construct pressure-volume profiles. Any differences between the profiles obtained during gastric distensions were evaluated by comparing areas under the curves (AUC).

Data were analyzed by ANOVA (analysis of variance), followed by post-hoc analysis, if statistically significant differences were obtained. Data are presented as means ±SEM (standard error of mean). Probability values of p <0.05 were regarded as statistically significant.

Responses During Duodenal Infusions

Infusion of an oil emulsion significantly increased gastric baseline volume (p <0.05). Addition of orlistat completely abolished the volume change during infusions (p <0.05).

Responses During Gastric Distensions

The orlistat-containing emulsion caused significantly less increase of intragastric volume during gastric distensions (p <0.05), (as shown by AUCs, gastric volume at MDP +4 mmHg and the slope of the p-V curve) than fat infusion alone (table 2).

TABLE 2

Pressure-volume relationships during gastric distensions and duodenal infusion of the fat

|  | LCT | LCT-orlistat |
|---|---|---|
| AUC (mmHg.ml) | 1388 ± 75* | 516 ± 54 |
| Volume at MDP + 4 mmHg(ml) | 533 ± 25* | 245 ± 25 |
| Slope (ml/mmHg) | 94 ± 6* | 52 ± 5 |

LCT: soybean oil.
Data are means ± SEM.
*Indicates a significance difference in pressure-volume relationships, after statistical analysis, in comparisson to corresponding orlistat treatment ($p < 0.05$).

Increasing intragastric pressure resulted in an increase of scores for fullness, bloating, nausea and pressure, and a decrease of scores for hunger during all duodenal infusions. The changes were pronounced during fat infusion (indicated by the slope of the pressure-score curves, by the scores at MDP +4 mmHg and also by the AUCs ). The effects of LCTs were significantly diminished by orlistat, suggesting that triglyceride digestion products are required for the induction of postprandial sensations and symptoms.

TABLE 3

Parameters characterising symptoms during gastric distensions and duodenal infusion of the fat emulsions.

|  | LCT | LCT-orlistat |
|---|---|---|
| AUC (mmHg) | | |
| Bloating | 7.1 ± 1.1* | 3.5 ± 0.6 |
| Fullness | 16.7 ± 1.1* | 10.9 ± 1.0 |
| Hunger | 11.9 ± 1.3* | 19.6 ± 1.4 |
| Nausea | 10.5 ± 1.3* | 1.8 ± 0.6 |
| Pressure/pain | 9.2 ± 1.3* | 5.8 ± 0.8 |
| Score at MDP + 4 mmHg | | |
| Bloating | 2.8 ± 0.4* | 1.3 ± 0.2 |
| Fullness | 5.8 ± 0.4* | 3.8 ± 0.3 |
| Hunger | 1.7 ± 0.3* | 4.3 ± 0.4 |
| Nausea | 4.5 ± 0.5* | 0.9 ± 0.2 |
| Pressure/pain | 3.8 ± 0.4* | 2.5 ± 0.3 |
| Slope (1/mmHg) | | |
| Bloating | 0.5 ± 0.1* | 0.2 ± 0.0 |
| Fullness | 0.8 ± 0.1* | 0.5 ± 0.1 |
| Hunger | −0.7 ± 0.1* | −0.3 ± 0.0 |
| Nausea | 0.9 ± 0.1* | 0.2 ± 0.0 |
| Pressure/pain | 0.6 ± 0.1 | 0.5 ± 0.1 |

LCT: soy bean oil.
Data are means ± SEM.
*Significant differences from respective orlistat condition, $p < 0.05$.

The maximally tolerated pressure during gastric distension during duodenal fat infusion was significantly increased by orlistat (e.g. $p < 0.05$).

Pharmaceutical Compositions

A)

| Ingredient | Quantity mg/Capsule |
|---|---|
| Orlistat | 120.00 |
| Microcrystalline Cellulose (AVICEL PH-101) | 93.60 |
| Sodium Starch Glycolate (PRIMOJEL) | 7.20 |
| Sodium Lauryl Sulfate | 7.20 |
| Polyvinylpyrrolidone (Povidone (K-30)) | 12.00 |
| Purified Water* | — |
| Talc | 0.24 |
| Total | 240.24 mg |

*Removed during processing

Procedure:
1. Blend orlistat, microcrystalline cellulose, and sodium starch glycolate in a suitable mixer.
2. Granulate with a solution of polyvinylpyrrolidone and sodium lauryl sulfate in purified water.
3. Pass the granulation through an extruder and pass the extrudate through a spheronizer to form pellets.
4. Dry the pellets at 30° C.
5. Add talc and mix.
6. Fill into hard gelatin capsules.

| Ingredient | Quantity mg/Capsule |
|---|---|
| Orlistat | 60 |
| Microcrystalline Cellulose | 46.8 |
| Sodium Starch Glycolate | 3.6 |
| Sodium Lauryl Sulfate | 3.6 |
| Polyvinylpyrrolidone | 6.0 |
| Purified Water* | — |
| Talc | 0.12 |
| Total | 120.12 mg |

*Removed during processing.

1. Blend orlistat, microcrystalline cellulose, and sodium starch glycolate in a suitable mixer.
2. Granulate with solution of polyvinyl pyrrolidone and sodium lauryl sulfate in purified water.
3. Pass the granulation through an extruder and pass the extrudate through a spheronizer to form pellets.
4. Dry the pellets at 30° C.
5. Add talc and mix.
6. Fill into hard gelatin capsules.

| Ingredient | Quantity mg/Capsule | |
|---|---|---|
| Orlistat | 60 | 120 |
| Lactose | 40 | 80 |
| Microcrystalline Cellulose | 60 | 120 |
| Sodium Lauryl Sulfate | 5.7 | 11.4 |
| Sodium Starch Glycolate | 20 | 40 |
| Polyvinylpyrrolidone | 10 | 20 |
| Purified Water* | | |
| Talc | 0.2 | 0.4 |
| Total | 195.9 mg | 391.8 mg |

*Removed during processing.

Procedure:
1. Blend orlistat, lactose, microcrystalline cellulose and sodium starch glycolate in a suitable mixer.
2. Granulate with a solution of polyvinylpyrollidone and sodium lauryl sulfate in purified water.

3. Pass the granulation through an extruder, and pass the extrudate through a spheronizer to form pellets.
4. Dry the pellets at 30° C.
5. Add talc and mix.
6. Fill into hard gelatin capsules.

What is claimed is:

1. A method for treating or reducing functional dyspepsia, which comprises administrating to a mammal an effective amount of a gastrointestinal lipase inhibitor selected from the group consisting of orlistat, lipstatin, panclicins, 2-oxy-4H-3,1-benzoxazin-4-ones and pharmaceutically acceptable salts thereof.

2. A method of reducing intensity of fullness, nausea, bloating or gastric distress following ingestion of fat rich meals or fat rich foods comprising administering to a human an effective amount of a gastrointestinal lipase inhibitor selected from the group consisting of orlistat, lipstatin, panclicins, 2-oxy-4H-3,1- benzoxazin-4-ones, and pharmaceutically acceptable salts thereof.

3. The method of claim 1, wherein the mammal is a human and the lipase inhibitor is orlistat.

4. The method of claim 2, wherein the lipase inhibitor is orlistat.

5. The method according to claim 3, wherein the lipase inhibitor is administered orally.

6. The method of claim 4 wherein the lipase inhibitor is administered orally.

7. The method of claim 5, wherein the amount of orlistat administered is from about 60 mg to about 360 mg per day.

8. The method of claim 6, wherein the amount of orlistat administered is from about 60 mg to about 360 mg per day.

9. The method of claim 7, wherein the orlistat is administered in three daily doses.

10. The method of claim 8, wherein the orlistat is administered in three daily doses.

11. The method of claim 7, wherein the amount of orlistat administered daily is 360 mg.

12. The method of claim 8 wherein the amount of orlistat administered daily is 360 mg.

13. The method of claim 1, which comprises treating functional dyspepsia by administrating to a mammal an effective amount of a gastrointestinal lipase inhibitor selected from the group consisting of orlistat, lipstatin, panclicins, 2-oxy-4H-3, 1- benzoxazin-4-ones, and pharmaceutically acceptable salts thereof.

14. The method of claim 13, wherein the gastrointestinal lipase inhibitor is orlistat.

15. The method of claim 14, wherein the orlistat is administered orally.

16. The method of claim 15, wherein the orlistat is administered in an amount of from about 60 mg to about 360 mg per day.

* * * * *